(12) United States Patent
Niitsu et al.

(10) Patent No.: US 9,914,983 B2
(45) Date of Patent: Mar. 13, 2018

(54) APOPTOSIS-INDUCING AGENT

(71) Applicant: Nitto Denko Corporation, Ibaraki-shi, Osaka (JP)

(72) Inventors: Yoshiro Niitsu, Sapporo (JP); Hiroki Nishita, Ibaraki (JP); Hiroyuki Tanaka, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 14/653,218

(22) PCT Filed: Dec. 20, 2013

(86) PCT No.: PCT/JP2013/084225
§ 371 (c)(1),
(2) Date: Jun. 17, 2015

(87) PCT Pub. No.: WO2014/098210
PCT Pub. Date: Jun. 26, 2014

(65) Prior Publication Data
US 2015/0328248 A1 Nov. 19, 2015

(30) Foreign Application Priority Data

Dec. 20, 2012 (JP) ................. 2012-278706

(51) Int. Cl.
| | | |
|---|---|---|
| C07H 21/04 | (2006.01) |
| A61K 45/06 | (2006.01) |
| A61K 31/7088 | (2006.01) |
| A61K 31/7105 | (2006.01) |
| A61K 31/713 | (2006.01) |
| C12N 15/113 | (2010.01) |

(52) U.S. Cl.
CPC .. *C12Y 205/01018* (2013.01); *A61K 31/7088* (2013.01); *A61K 31/713* (2013.01); *A61K 31/7105* (2013.01); *A61K 45/06* (2013.01); *C12N 15/1137* (2013.01); *C12N 2310/14* (2013.01)

(58) Field of Classification Search
CPC .................................... C07H 21/04
See application file for complete search history.

(56) References Cited

U.S. PATENT DOCUMENTS

| | | | |
|---|---|---|---|
| 4,966,773 A | 10/1990 | Gressel et al. |
| 5,643,584 A | 7/1997 | Farng et al. |
| 5,811,119 A | 9/1998 | Mehta et al. |
| 5,851,538 A | 12/1998 | Froix et al. |
| 6,183,774 B1 | 2/2001 | Aust et al. |
| 6,627,732 B1 | 9/2003 | Sakon et al. |
| 8,173,170 B2 | 5/2012 | Niitsu et al. |
| 8,178,124 B2 | 5/2012 | Niitsu et al. |
| 8,574,623 B2 | 11/2013 | Niitsu et al. |
| 8,652,526 B2 | 2/2014 | Niitsu et al. |
| 8,686,052 B2 | 4/2014 | Niitsu et al. |
| 2002/0012998 A1 | 1/2002 | Gonda et al. |
| 2003/0096739 A1 | 5/2003 | Morris |
| 2003/0161791 A1 | 8/2003 | Bentley et al. |
| 2003/0211143 A1 | 11/2003 | Liu et al. |
| 2004/0018985 A1 | 1/2004 | Sakon et al. |
| 2004/0028682 A1 | 2/2004 | Border et al. |
| 2004/0029275 A1* | 2/2004 | Brown ................. C12N 15/111 435/375 |
| 2004/0037833 A1 | 2/2004 | Mather et al. |
| 2004/0171814 A1 | 9/2004 | Mather et al. |
| 2005/0004064 A1 | 1/2005 | Tei et al. |
| 2005/0152907 A1 | 7/2005 | Liang et al. |
| 2005/0165227 A1 | 7/2005 | Vlahov et al. |
| 2006/0013775 A1 | 1/2006 | Gristwood et al. |
| 2006/0074041 A1 | 4/2006 | Johnston et al. |
| 2008/0057030 A1 | 3/2008 | Crager |
| 2008/0207553 A1 | 8/2008 | Zhao et al. |
| 2008/0279765 A1 | 11/2008 | Chettibi et al. |
| 2008/0312174 A1 | 12/2008 | Yu et al. |
| 2009/0105179 A1 | 4/2009 | Yu et al. |
| 2010/0028416 A1 | 2/2010 | Yu et al. |
| 2010/0144659 A1 | 6/2010 | Niitsu et al. |
| 2011/0104255 A1 | 5/2011 | Niitsu et al. |
| 2011/0178157 A1 | 7/2011 | Jin et al. |
| 2011/0229558 A1 | 9/2011 | Niitsu et al. |
| 2012/0269886 A1 | 10/2012 | Niitsu et al. |
| 2012/0328694 A1 | 12/2012 | Niitsu et al. |
| 2013/0011336 A1 | 1/2013 | Niitsu et al. |

(Continued)

FOREIGN PATENT DOCUMENTS

| | | |
|---|---|---|
| CN | 1953762 A | 4/2007 |
| EP | 1842557 | 10/2007 |

(Continued)

OTHER PUBLICATIONS

Mochizuki et al. (Oncogene 2002, p. 3699-3707).*
Kondo et al. Kondo 1 (Nature Reviews/Cancer 2005, vol. 5: 726-734).*
Maiuri et al. (Cell Death and Differentiation 2009, 16: 87-93).*
Li et al. (Autophagy 4:1 2008: 54-60).*
Kondo et al. referred to as Kondo 2 (Autophagy 2006: 85-90).*
Ito et al Igaku Shoin's Medical Dictionary Mar. 2003, 1st Edition, 654-655.
Swami "Akt: a double-edged sword" Nature Reviews Cancer published online Dec. 29, 2008, pp. 76-77.
Office Action dated Jul. 4, 2016 for JP 2012-278706.
Andrew, E.R., et al., "Molecular motion in solid all-trans retinoic acid (vitamin A acid) by proton NMR." Solid State Nuclear Magnetic Resonance 13, pp. 39-43, 1998.
Barnett et al "Identification and characterization of pleckstrin-homology-domain-dependent and isoenzyme-specific Akt inhibitors" 2005 Biochem Journal 385 vol. 399-408.

(Continued)

*Primary Examiner* — Kimberly Chong
(74) *Attorney, Agent, or Firm* — Knobbe, Martens, Olson & Bear, LLP

(57) ABSTRACT

The purpose of the present invention is to provide a composition for effectively inducing apoptosis and/or proliferation inhibition in a cell, and a method using the same. An agent for inducing apoptosis that comprises as active ingredients a drug inhibiting GST-π and a drug inhibiting Akt; a medicinal composition comprising the same; a method for treating a disease caused by abnormality in apoptosis using the same, etc.

2 Claims, 3 Drawing Sheets

(56) References Cited

U.S. PATENT DOCUMENTS

| | | | |
|---|---|---|---|
| 2013/0045272 | A1 | 2/2013 | Niitsu et al. |
| 2013/0064815 | A1 | 3/2013 | Coller |
| 2013/0136789 | A1 | 5/2013 | Niitsu et al. |
| 2013/0171127 | A1 | 7/2013 | Niitsu et al. |
| 2013/0171240 | A1 | 7/2013 | Niitsu et al. |
| 2013/0172401 | A1 | 7/2013 | Niitsu et al. |
| 2013/0210744 | A1 | 8/2013 | Niitsu et al. |
| 2013/0216611 | A1 | 8/2013 | Niitsu et al. |
| 2013/0267581 | A1 | 10/2013 | Niitsu et al. |
| 2014/0127187 | A1 | 5/2014 | Niitsu et al. |
| 2014/0315975 | A1 | 10/2014 | Niitsu et al. |
| 2014/0323550 | A1 | 10/2014 | Ayabe et al. |

FOREIGN PATENT DOCUMENTS

| | | |
|---|---|---|
| JP | 08-268906 | 10/1996 |
| JP | 11-269076 | 10/1999 |
| JP | 2002-047211 | 2/2002 |
| JP | 2002-363094 | 12/2002 |
| JP | 2002-371006 | 12/2002 |
| JP | 2003-119138 | 4/2003 |
| JP | 2003-219893 | 8/2003 |
| JP | 2005-532050 | 10/2005 |
| JP | 2006-506071 | 2/2006 |
| JP | 2007-529197 | 10/2007 |
| JP | 2009-542723 | 12/2009 |
| WO | WO 91/04748 | 4/1991 |
| WO | WO 95/08563 | 3/1995 |
| WO | WO 96/40205 | 12/1996 |
| WO | WO 99/54346 | 10/1999 |
| WO | WO 00/64478 | 11/2000 |
| WO | WO 03/009881 | 2/2003 |
| WO | WO 03/045383 | 6/2003 |
| WO | WO 2004/001381 | 12/2003 |
| WO | WO 2004/019921 | 3/2004 |
| WO | WO 2004/043239 | 5/2004 |
| WO | WO 2004/069159 | 8/2004 |
| WO | WO 2004/090108 | 10/2004 |
| WO | WO 2005/028498 | 3/2005 |
| WO | WO 2005/082402 | 9/2005 |
| WO | WO 2005/112973 | 12/2005 |
| WO | WO 2006/068232 | 6/2006 |
| WO | WO 2006/078774 | 7/2006 |
| WO | WO 2008/006040 | 1/2008 |
| WO | WO 2008/120815 | 10/2008 |
| WO | WO 2009/036368 | 3/2009 |
| WO | WO 2010/014117 | 2/2010 |
| WO | WO 2012/170952 | 12/2012 |
| WO | WO 2012/176282 | 12/2012 |

OTHER PUBLICATIONS

Beljaars, L., et al. "Albumin Modified With Mannosa 6-Phosphate: A Potential Carrier for Selective Delivery of Antifibrotic Drugs to Rat and Human Hepatic Stellate Cells." Hepatology vol. 29, No. 5, pp. 1486-1493, 1999.

Blomhoff et al., "Hepatic Uptake of [H] Retinol Bound to the Serum Retinol Binding Protein Involves Both Parenchymal and Perisinusoidal Stellate Cells, " The Journal of Biological Chemistry 1985; 260(25): 13571-13575.

Blomhoff, Rune, et al., Newly Administered [$^3$H] Retinol is Transferred from Hepatocytes to Stellate Cells in Liver for Storage. Experimental Cell Research, vol. 150, pp. 186-193, 1984.

Devi, GR. "siRNA-based Approaches in Cancer Therapy", Cancer Gene Therapy (2006) 13, 819-29.

Dixon et al., "Nomenclature of Retinoids." Pure & Appl. Chem., vol. 55, No. 4, pp. 721-726 (1983).

Dunham et al., Membrane fusion: Studies with a calcium-sensitive dye, arsenazo III, in liposomes. Proceedings of the National Academy of Science, USA, vol. 74, No. 4, pp. 1580-1584, 1997.

Fortuna V.A. et al., "Hepatic Stellate Cells Uptake of Retinol Associated With Retinol-Binding Protein or With Bovine Serum Albumin," Journal of Cellular Biochemistry 2003; 90(4):792-805.

Friedman, S. L., "Targeting siRNA to arrest fibrosis," Nature Biotechnology (Apr. 2008) 26(4): 399-400.

Goodman et al., "Extraction and Recombination Studies of the Interaction of Retinol with Human Plasma Retinol-Binding Protein." Journal of Lipid Research, vol. 13, 1972, pp. 338-347.

Kamps, J.Aam. et al., "Massive targeting of liposomes, surface-modified with anionized albumins, to hepatic endothelial cells," Proceedings of the National Academy of Sciences USA 1997; 94(21):11681-11685.

Kang et al., "Mannose-6-phosphateyinsulin-like growth factor-II receptor is a retinoic acid." Proc. Natl. Acad. Sci., vol. 95, pp. 13671-13676, Dec. 1998.

Kikuchi, H., Liposomes based on nanotechnology. Past, present and future. Part II, Pharm Tech Japan 2003; 19(3):419-433.

Kim et al., "Folate-tethered emulsion for the target delivery of retinoids to cancer cells." European Journal of Pharmaceutics and Biopharmaceutics. 68:618-625. (2008).

Li, D. et al., "Liver fibrogenesis and the role of hepatic stellate cells: New insights and prospects for therapy," Journal of Gastroenterology and Hepatology 1999; 14(7):618-633.

Lim et al., "Formulation parameters determining the physicochemical characteristics of solid lipid nanoparticles loaded with all-trans retinoic acid." International Journal of Pharmaceutics. 243:135-146. (2002).

Lindsley, et al., Allosteric Akt (PKB) inhibitors: discovery and SAR of isozyme selective inhibitors, Bioorganic & Medicinal Chemistry Letter 15 (2005) 761-764.

Ma et al., "Comparison of Stability for All-trans Retinoic Acid Nanosuspensions and Lipid Nanoparticle Formulations." International Conference on Complex Medical Engineering. 197-202. (2007).

Marcucci et al., "Active targeting with particulate drug carriers in tumor therapy: fundamentals and recent progress." Drug Discovery Today. 9(5):219-228. (2004).

Nastruzzi et al., "Liposome-associated retinoic acid increased in vitro antiproliferative effects on neoplastic cells" FEBS Letters (1990) 259(2):293-296.

Sato et aL, "Resolution of liver cirrhosis using vitamin A-coupled liposomes to deliver siRNA against a collagen-specific chaperone", Nature Biotechnology (2008) 26(4):431-442.

Singh, et al. "Liposome encapsulated vitamin A compounds exhibit greater stability and diminished toxicity." Biophysical Chemistry, vol. 73, pp. 155-162, 1998.

Socaciu, et al., Different Ways to Insert Carotenoids into Liposomes Affect Structure and Dynamics of the Bilayer Differently. Biophysical Chemistry, vol. 99, pp. 1-15, 2002.

Torchilin et al., "Immunomicelles: Targeted pharmaceutical carriers for poorly soluble drugs." PNAS. 100(10):6039-6044. (2003).

Torchilin, V. P. "Drug Targeting," European Journal of Pharmaceutical Sciences. (2000) 11(2):81-91.

Tsuji, H. et al., "Targeting of liposomes surface-modified with glycyrrhizin to the liver. I. Preparation and biological disposition," Chemical & Pharmaceutical Bulletin 1991; 39(4):1004-08.

Vogel et al., "An immortalized rat liver stellate cell line (HSC-TS): a new cell model for the study of retinoid metabolism in vitro." Journal of Lipid Research, vol. 41, 2000, pp. 882-893.

Wassall, S.R., et al. "Retinoid-Phospholipid Interactions as Studied by Magnetic Resonance" Bulletin of Magnetic Resonance, vol. 9 No. 3, pp. 85-89, 1987.

Watanabe, et al., Treatment of idiopathic myelofiosis employing siRNA for heat shock protein 7 (siRNA/HSP47) encapsulated in liposomes, Blood (2007) 110:235.

Whitmer et al., Membrane-membrane interactions associated with rapid transfer of liposomal bilirubin to microsomal UDP-glucuronyltransferase. Biochemical Journal, vol. 244, pp. 41-47, 1987.

Wu, J. et al., "Modification of liposomes for liver targeting," Journal of Hepatology (1996)24(6):757-763.

Zhang et al., "Cationic lipids and polymers mediated vectors for delivery of siRNA," J. Control Release (2007) 123: 1-10.

Zhao, et al., "Discovery of 2,3,5-trisubstituted pyridine derivatives as potent AKt1 and Akt2 dual inhibitors", Bioorganic & Medicinal Chemistry Letters 15 (2005) 905-909.

(56) References Cited

OTHER PUBLICATIONS

Zhao et al.; "Tumor-selective targeted delivery of genes and antisense oligodeoxyribonucleotides via the folate receptor," Advanced Drug Delivery Reviews (2004) 56: 1193-1204.
Ban et al., "Transfection of Glutathione S-Transferase (GST)-π Antisense Complementary DNA Increases the Sensitivity of a Colon Cancer Cell Line to Adriamycin, Cisplatin, Melphalan, and Etoposide" Cancer Research (1996) 56:3577-3582.
Futreal et al., "A Census of Human Cancer Genes" Nat. Rev. Cancer (2004) 4(3):177-183.
Hall et al., "Possible Role of Inhibition of Glutathione S-transferase in the Partial Reversal of Chlorambucil Resistance by Indomethacin in a Chinese Hamster Ovary Cell Line"Cancer Research (1989) 49:6265-6268.
Hokaiwado et al., "Glutathione S-transferase Pi mediates proliferation of androgen-independent prostate cancer cells" Carcinogenesis (2008) 29(6):1134-1138.
Klionsky et al., "A Unified Nomenclature for Yeast Autophagy-Related Genes" Developmental Cell (2003) 5:539-545.
Nagaprashantha et al., "2'-Hydroxyflavanone inhibits proliferation, tumor vascularization and promotes normal differentiation in VHL-mutant renal cell carcinoma" Carcinogenesis (2011) 32(4):568-575.
Nakajima et al., "Reversal of Multiple Drug Resistance in Cholangiocarcinoma by the Glutathione S-transferase-π-Specific Inhibitor $O^1$-Hexadecyl-γ-glutamy-S-benzylcysteinyl-D-phenylglycine Ethylester" The Journal of Pharmacology and Experimental Therapeutics (2003) 306(3):861-869.
Nishita et al., "Abstract 1065: Regulation of autophagy and MAPK signaling by glutathione S-transferase-nin KRAS mutated cancer cells" Cancer Research (2011) 71(8):AM2011-1065.
Pirollo et al, "Targeted Delivery of Small Interfering RNA: Approaching Effective Cancer Therapies" Cancer Research (2008) 68(5):1247-50.
Ruoslahti et al., "Targeting of drugs and nanoparticles to tumors" J. Cell. Biol. (2010) 188(6):759-68.
Takahashi et al, "Glutathione S transferases-pi" Gan to Kagaku Ryoho (1994) 21(7):945-951 (Abstract Only).
Tew et al., "Ethacrynic Acid and Piriprost as Enhancers of Cytotoxicity in Drug Resistance and Sensitive Cell Lines" Cancer Research (1988) 48:3622-3625.
Torchilin et al., "Targeted pharmaceutical nanocarriers for cancer therapy and imaging" AAPS J. (2007) 9(2):E128-47.
Yang et al., "Mammalian autophagy: core molecular machinery and signaling regulation" Current Opinion in Cell Biology (2010) 22:124-131.
International Search Report and Written Opinion dated Apr. 8, 2014 for PCT Application No. PCT/JP2013/084225, filed Dec. 20, 2013.
International Preliminary Report on Patentability dated Jun. 23, 2015 for PCT Application No. PCT/JP2013/084225, filed Dec. 20, 2013.
Extended European Search Reported, in European Application No. 13865094, dated Jun. 28, 2016.
Pal, Akt inhibitors in clinical development for the treatment of cancer, Expert Opinion on Investigation Drugs, vol. 19, No. 11, Nov. 1, 2010, pp. 1355-1366.
Kondo et al Autophagy in Cancer, Feb. 2006, Ishiyaku Publishers, Inc., vol. 216, No. 7, 525-529, dated.
Thimmaiah, et al., Identification of $N^{10}$-Substituted Phenoxazines as Potent and Specific Inhibitors of Akt Signaling, The Journal of Biological Chemistry, Sep. 9, 2005, vol. 280, No. 36, p. 31924-31935.
Lee, et al., Roles of AKT1 and AKT2 in non-small cell lung cancer cell survival, growth, and migration, Cancer Science, Oct. 2011, vol. 102, No. 10, p. 1822-1828.
Office Action in Japanese Patent Application No. 2012-278706, dated Dec. 15, 2016, with English Translation.
Takayama et al "Chemoprevention of colorectal cancer targeting GST-pi" Frontiers in Gastroenterology, Jan. 2010, vol. 15, No. 1, p. 11-17.

Uchida, et al., MiR-133a induces apoptosis through direct regulation of GSTP1 in bladder cancer cell lines, Urologic Oncology. [online], Mar. 10, 2011, vol. 31, Issue 1, p. 115-123, internet <DOI:10.1016/j.urolonc.2010.09.017>.
Mandal, M. et al., "The Akt inhibitor KP372-1 suppresses Akt activity and cell proliferation and induces apoptosis in thyroid cancer cells," British Journal of Cancer (2005) 92, pp. 1899-1905.
Chinese Office Action dated Mar. 23, 2017 for Chinese Application No. 201380067175.8.
Amaravadi et al., "Autophagy inhibition enhances therapy-induced apoptosis in a Myc-induced model of lymphoma" J. Clin. Invest. (2007) 117:326-336.
Bae et al., Suppression of Autophagy by FIP200 Deletion Impairs DNA Damage Repair and Increases Cell Death upon Treatments with Anticancer Agents, Molecular Cancer Research, 2011, 9(9), p. 1232-1241.
Bos, ras Oncogenes in Human Cancer: A Review, Cancer Research, 1989;49(17):4682-9.
Chano et al., Identification of RB1CC1, a novel gene that can induce RB1 in various human cells, Oncogene. 2002;21(8):1295-8.
Chano et al., RB1CC1 insufficiency causes neuronal atrophy through mTOR signaling alteration and involved in the pathology of Alzheimer's diseases, Brain Res., 2007, 1168, p. 97-105.
Eickelmann et al., "Expression of NAD(P)H: quinone oxidoreductase and glutathione S-transferases alpha and pi in human renal cell carcinoma and in kidney cancer-derived cell lines", Carcinogenesis, Feb. 1994; 15(2): 219-25.
Fesik et al., Promoting Apoptosis as a Strategy for Cancer Drug Discovery, Nature Reviews, vol. 5, Nov. 2005, p. 876-885.
Gao et al., "Autophagy negatively regulates Wnt signaling by promoting Dishevelled degradation" Nature Cell Biology (2010) 12(8):781-790 with Supplementary Information 1-8.
Gedaly et al., Pi-103 and Sorafenib Inhibit Hepatocellular Carcinoma Cell Proliferation by Blocking Ras/Raf/MAPK and PI3K/AKT/mTOR Pathways, Anticancer Research (2010) 30:4951-4958.
Ikeda et al., Inhibition of Autophagy Enhances Sunitinib-Induced Cytotoxicity in Rat Pheochromocytoma PC12 cells, Journal Pharmacological Sciences, 2013, 121(1), p. 67-73.
Katopodis et al., "MG-63 Osteoblast-like Cells Enhance the Osteoprotegerin Expression of PC-3 Prostate Cancer Cells." Anticancer Research, 2009, pp. 4013-4018, vol. 29.
Kim et al., "Anti-tumor Activity of the Ginsenoside Rk1 in Human Hepatocellular Carcinoma Cells through Inhibition of Telomerase Activity and Induction of Apoptosis", Biol. Pharm. Bull. 31(5) 826-830, vol. 31, No. 5 (2008).
Ko et al., Autophagy Inhibition Enhances Apotosis Induced by Ginsenoside Rk1 in Hepatocellular Carcinoma Cells, Biosci. Biotechnol. Biochem. (2009) 73(10):2183-2189.
Kondo et al., The Role of Autophagy in Cancer Development and Response to Therapy, Nature Reviews, vol. 5, Sep. 2005, p. 726-734.
Kozlowski, et al. "Metastatic Behavior of Human Tumor Cell Lines Grown in the Nude Mouse." Cancer Research, 1984, pp. 3522-3529, vol. 44.
Levi et al., Multiple K-ras Codon 12 Mutations in Cholangiocarcinomas Demonstrated with a Sensitive Polymerase Chain ReactionTechnique, Cancer Research, 1991;51(13):3497-3502.
Li, et al., Autophagy protects LNCaP Cells under androgen deprivation conditions, Autophagy 4:1, 54-60, Jan. 1, 2008.
Li et al., FIP200 is Involved in Murine Pseudomonas Infection by Regulating HMGB1 Intracellular Translocation, Cell Physiol. Biochem., 2014.5, 33(6), p. 1733-1744.
Maiuri et al., Control of autophagy by oncogenes and tumor suppressor genes, Cell Death and Differentiation (2009) 16, 87-93.
Miyanishi et al., "Glutathione S-Transferase-⊐ Overexpression is Closely Associated with K-ras Mutation During Human Colon Carcinogenesis" *Gastroenterology* (2001) 121(4):865-874.
Miyazawa et. al., "Induction of autophagy and apoptosis in leukemia cells by vitamin K2" vol. 48, No. 9, 2007, p. 1097, Dai 69 Kai The Japanese Society of Hematology, Dai 49 Kai The Japanese Society of Clinical Hematology Godo Sokai Program Shorokushu.

(56) References Cited

OTHER PUBLICATIONS

Mochizuki et al., Inhibition of NADPH oxidase 4 activates apoptosis via the AKT/apoptosis signal-regulating kinase 1 pathway in pancreatic cancer PANC-1 cells, Oncogene (2006)25, 3699-3707.
Nagaprashantha et al., "2'-Hydroxyflavanone inhibits proliferation, tumor vascularization and promotes normal differentiation in VHL-mutant renal cell carcinoma" Carcinogenesis (2011) 32(4):568-575.
Nishimura et al., RB1CC1 Protein Suppresses Type II Collagen Syntheis in Chondrocytes and Causes Dwarfism, the Journal Biological Chemistry, 2011, 286(51), p. 43925-43932.
Nishita, Hiroki et al, "GSTP1 enhances Raf-1/MEK/ERK pathway by preventing proteasomal degradation of Raf-1 in human colon cancer cells", Report of the 69th Annual Meeting of the Japanese Cancer Association (Aug. 23, 2010) p. 211.
Nobuoka et al, "Glutathione-S-Transferase P1-1 Protects Aberrant Crypt Foci From Apoptosis Induced by Deoxycholic Acid" Gastroenerology 127:428-433 2004.
Nobs et al., Current Methods for Attaching Targeting Ligands to Liposomes and Nanoparticles, Journal of Pharmaceutical Sciences, 2004;93(8):1980-1992.
Park et al., Properties of circular dumbbell RNA/DNA chimeric oligonucleotides containing antisense phosphodiester oligonucleotides, Nucleic Acids Symposium Series 1999;(42):225-226.
Payne et al, "Deoxycholate, an Endogenous Cytotoxin/Genotoxin, Induces the Authophagic Stress-Survival Pathway: Implications for Colon Carcinogensis" Journal of Toxicology vol. 2009, Article 785907, 14 pages, 2009.
Scharmach et al. "Glutathione S-transferase expression and isoenzyme composition during cell differentiation of Caco-2 cells", Toxicology. Nov, 30, 2009;265(3):122-26. doi: 10.1016/j.tox.2009.09.017. Epub Oct. 1, 2009.
Sun et al. "Bioluminescent imaging study; FAK inhibitor, PF-562,271, preclinical study in PC3M-luc-C6 local implant and metastasis xenograft models." Cancer Biology and Therapy, 2010, pp. 1-6, vol. 10:1.
Takanashi et al., The role of GSTpi as a mediator of Map kinase in colon carcinogenesis, Proceeding of the Japanese Cancer Association, 2007 vol. 66, p. 181.
Torchilin, Recent Advances With Liposomes as Pharmaceutical Carriers, Natural Reviews Drug Discovery, 2005;4(2)145-160.
Tsukamoto et. al., "Tenkai Suru Proteasome Sogaizai Kenkyu", Experimental Medicine, 2008, vol. 26, No. 2, pp. 242 to 247.
Wee et al. "P13K Pathway Activation Mediates Resistance to MEK Inhibitors in KRAS Mutant Cancers." Cancer Research, 2009, pp. 4286-4293, vol. 69.
Wei et al., p62/SQSTM1 synergizes with autophagy for tumor growth in vivo, Genes Development, 2014, 28(11), p. 1204-1216.
Yao et al., Deletion of autophagy inducer RB1CC1 results in degeneration of the retinal pigment epithelium, Autophagy, 2015, 11(6), p. 939-953.
Yoo et al., "Oncogenic ras-induced Down-regulation of Autophagy Mediator Beclin-1 Is Required for Malignant Transformation of Intestinal Epithelial Cells," The Journal of Biological Chemistry, vol. 285, No. 8, pp. 5438-5449, Feb. 19, 2010.
International Search Report and Written Opinion dated Sep. 13, 2011 for PCT Application No. PCT/JP2011/064163, filed Jun. 21, 2011.
Office Action in Japanese Patent Application No. 2012-278706 dated Aug. 3, 2017, with English machine translation.

* cited by examiner

[Fig. 1]
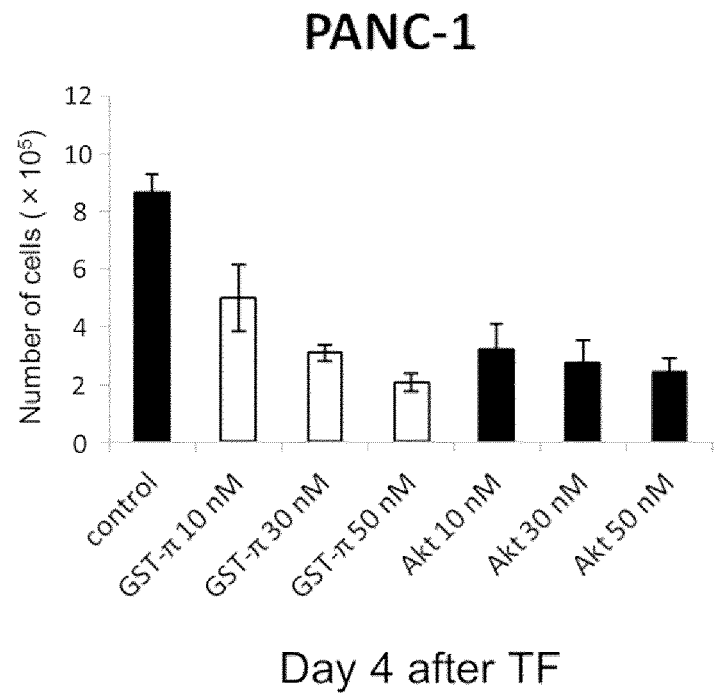
[Fig. 2]
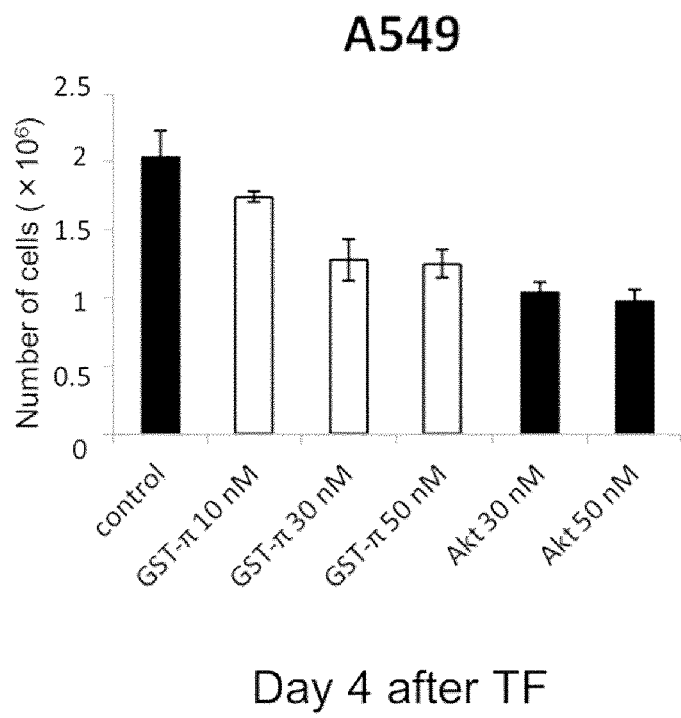

[Fig. 3]
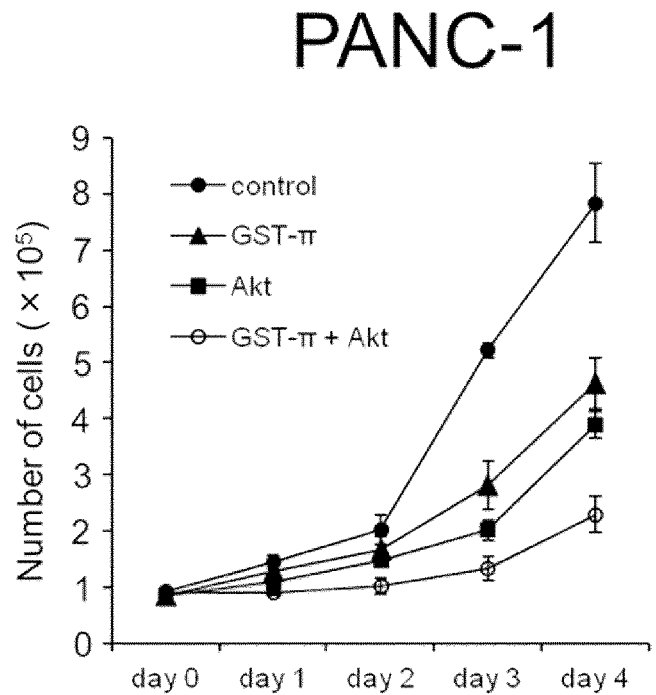
[Fig. 4]
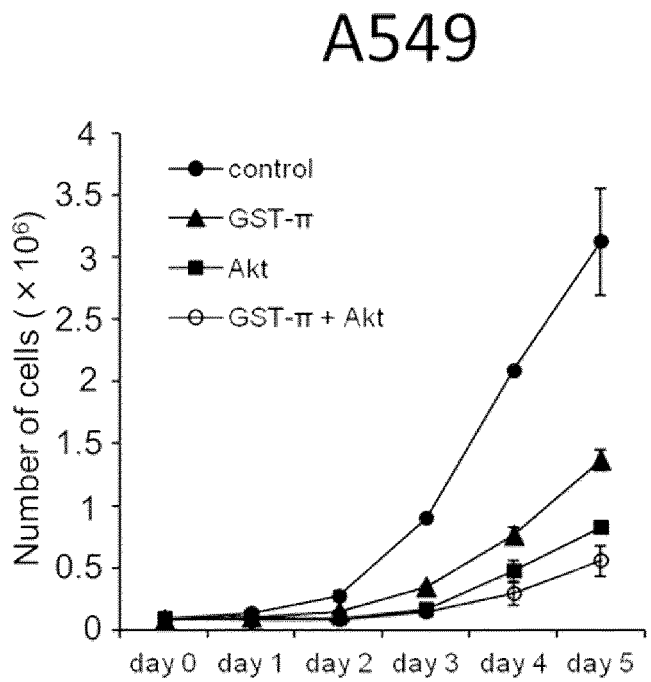

[Fig. 5]
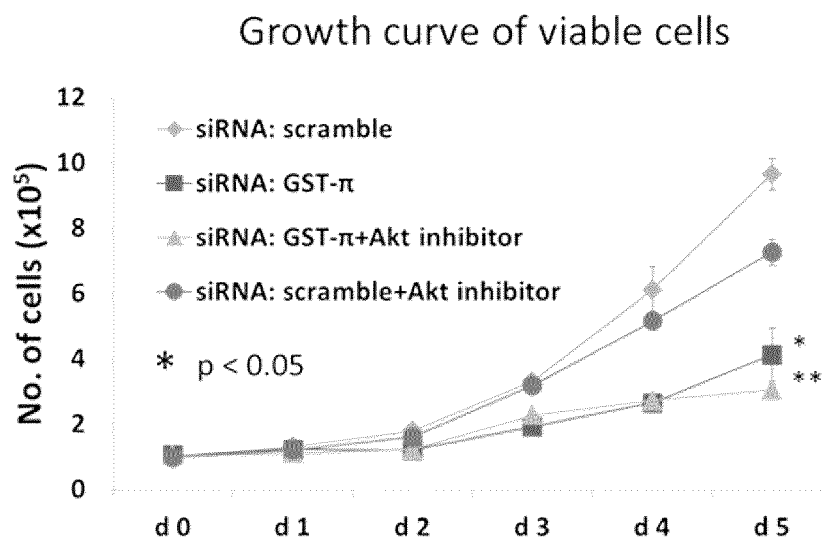
[Fig. 6]
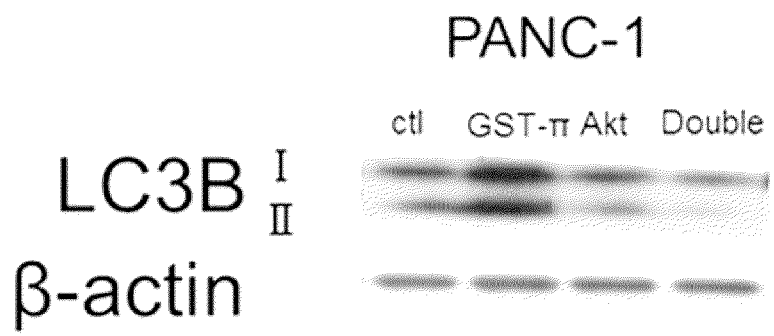

APOPTOSIS-INDUCING AGENT

TECHNICAL FIELD

The present invention relates to a novel apoptosis-inducing agent, a novel cell proliferation-suppressing agent, a novel autophagy-suppressing agent, a pharmaceutical composition containing the apoptosis-inducing agent, cell proliferation-suppressing agent, or autophagy-suppressing agent, and a novel therapeutic method for a disease associated with abnormal apoptosis, cell proliferation, or autophagy.

BACKGROUND ART

Cancer is one of the most important and troublesome diseases that confront mankind, and an enormous amount of research effort into the treatment thereof is being carried out. Cancer is a disease in which cells grow uncontrollably due to gene mutation, epigenetic abnormality, etc. With regard to genetic abnormalities in cancer, a large number have already been reported (e.g., Non-Patent Document 1, etc.), and it is thought that many thereof are somehow associated with signal transduction related to cell proliferation, differentiation, and survival. Furthermore, due to such genetic abnormalities, abnormalities occur in signal transduction in cells consisting of normal molecules, and this causes activation or inactivation of a specific signal cascade and can finally become one factor triggering abnormal cell proliferation. Early cancer treatment has focused on suppression of cell proliferation itself, but since such a treatment also suppresses proliferation of cells with physiologically normal proliferation, it was accompanied by side effects such as hair loss, gastrointestinal dysfunction, or bone marrow suppression. In order to reduce such side effects, development of drugs for the treatment of cancer based on a new concept such as molecularly targeted drugs that target cancer-specific genetic abnormalities or abnormalities in signal transduction is being undertaken.

Expression of glutathione-S-transferase (GST), which is one of the enzymes that catalyze glutathione conjugation, in particular GST-π (glutathione S-transferase pi, also called GSTP1), increases in various cancer cells, and it has been pointed out that there is a possibility that this is one factor for resistance to some anticancer agents. In fact, it is known that when GST-π antisense DNA or a GST-π inhibitor is made to act on a cancer cell line that is overexpressing GST-π and exhibiting drug resistance, the drug resistance is suppressed (Non-Patent Documents 2 to 4). Furthermore, in a recent report, when GST-π siRNA is made to act on an androgen-independent prostate cancer cell line that is overexpressing GST-π, proliferation thereof is suppressed and apoptosis is increased (Non-Patent Document 5). Moreover, it has been reported that, when GST-π siRNA is made to act on a cancer line that has a KRAS mutation, activation of Akt is suppressed, and autophagy increases, but there is only a medium degree of induction of apoptosis (Non-Patent Document 6).

However, there has so far been hardly any clarification of the relationship between GST-π and cell proliferation or apoptosis, the molecular mechanism of GST-π, and the role, etc., of GST-π in various types of intracellular signal transduction. Intracellular signal transduction is very complicated; one molecule may influence the effect of a plurality of molecules, or conversely one molecule may be influenced by a plurality of molecules, when the effect of a certain molecule is inhibited, another signal cascade may be activated, and an expected effect often cannot be obtained. Therefore, it is necessary to elucidate the complicated cell signal transduction mechanism in order to develop superior molecularly targeted drugs, but only a very small part of the mechanism has been elucidated in many years of research, and further research effort is needed.

PRIOR ART DOCUMENTS

Non-Patent Documents

Non-Patent Document 1: Futreal et al., Nat Rev Cancer. 2004; 4 (3): 177-83

Non-Patent Document 2: Takahashi and Niitsu, Gan To Kagaku Ryoho. 1994; 21 (7): 945-51

Non-Patent Document 3: Ban et al., Cancer Res. 1996; 56 (15): 3577-82

Non-Patent Document 4: Nakajima et al., J Pharmacol Exp Ther. 2003; 306 (3): 861-9

Non-Patent Document 5: Hokaiwado et al., Carcinogenesis. 2008; 29 (6): 1134-8

Non-Patent Document 6: Nishita et al., AACR 102nd Annual Meeting, Abstract No. 1065

SUMMARY OF THE INVENTION

Problems to be Solved by the Invention

It is an object of the present invention to provide a composition for inducing apoptosis and/or proliferation inhibition effectively in cells, and a method using same.

Means for Solving the Problems

While carrying out intensive research in order to elucidate the molecular mechanism of GST-π, the present inventors have found that when there is simultaneous inhibition of expression of GST-π and Akt, compared with a case in which expression of only one of the two is inhibited, cell proliferation is more strongly suppressed, and cell death is more strongly induced and also have found that autophagy, which is induced by inhibition of expression of GST-π, is markedly suppressed by simultaneously inhibiting expression of Akt, and the present invention has thus been accomplished.

That is, the present invention relates to the following.

(1) An agent for inducing apoptosis, the agent comprising as active ingredients a drug that suppresses GST-π and a drug that suppresses Akt.

(2) An agent for suppressing cell proliferation, the agent comprising as active ingredients a drug that suppresses GST-π and a drug that suppresses Akt.

(3) An agent for suppressing autophagy in a cell in which GST-π is suppressed, the agent comprising as an active ingredient a drug that suppresses Akt.

(4) An agent for enhancing the induction of apoptosis and/or the suppression of cell proliferation by a drug that suppresses GST-π, the agent comprising as an active ingredient a drug that suppresses Akt.

(5) The agent according to anyone of (1) to (4), wherein the active ingredient is selected from the group consisting of an RNAi molecule, a ribozyme, an antisense nucleic acid, a DNA/RNA chimera polynucleotide, and a vector expressing same.

(6) A pharmaceutical composition comprising the agent according to any one of (1) to (5).

(7) The pharmaceutical composition according to (6), the composition being for use in the treatment of a disease caused by abnormal cell proliferation.
(8) The pharmaceutical composition according to (6), the composition being for use in the treatment of a cancer.

Effects of the Invention

Since the apoptosis-inducing agent of the present invention can induce apoptosis and suppress cell proliferation more effectively compared with a conventional one, it is extremely useful as a pharmaceutical composition. In the treatment of cancer in particular, since cancer cells can be killed by apoptosis, not only is it possible to inhibit the progression of cancer, but an effect in making cancer regress can also be expected.

BRIEF DESCRIPTION OF DRAWINGS

FIG. 1 is a graph showing the effect of suppressing cell proliferation by knockdown of GST-π or Akt in PANC-1 cells.
FIG. 2 is a graph showing the effect of suppressing cell proliferation by knockdown of GST-π or Akt in A549 cells.
FIG. 3 is a graph showing the effect of suppressing cell proliferation by double knockdown of GST-π and Akt in PANC-1 cells.
FIG. 4 is a graph showing the effect of suppressing cell proliferation by double knockdown of GST-π and Akt in A549 cells.
FIG. 5 is a graph showing the effect of suppressing cell proliferation by the combined use of GST-π siRNA and Akt inhibitor. *P<0.05, **P<0.01.
FIG. 6 is a graph showing the effect of suppressing autophagy by double knockdown of GST-π and Akt.

MODES FOR CARRYING OUT THE INVENTION

The present invention relates to an agent or composition for suppressing cell proliferation (hereinafter, also called a 'cell proliferation-suppressing agent' or 'cell proliferation-suppressing composition') and an agent or composition for inducing apoptosis (hereinafter, also called an 'apoptosis-inducing agent' or an 'apoptosis-inducing composition') that contains as active ingredients a drug that suppresses GST-π and a drug that suppresses Akt.

When used herein, GST-π denotes an enzyme, encoded by GSTP1 gene, that catalyzes glutathione conjugation. GST-π is present in various animals, including humans, and its sequence information is known (e.g., human: NP_000843 (NM_000852), rat: NP_036709 (NM_012577), mouse: NP_038569 (NM_013541), etc. The numbers denote NCBI database accession numbers; those outside parentheses are amino acid sequence numbers, and those inside parentheses are base sequence numbers).

When used herein, Akt denotes serine/threonine kinase having a PH domain encoded by Akt gene. Akt is known to have three types of isotypes, Akt1 to 3; since the one that is involved in the PI3K/AKT/mTOR pathway is Akt1, in the present specification Akt means Akt1 unless otherwise specified. Akt is present in various animals, including humans, and its sequence information is known (e.g., human: NP_005154 (NM_005163), etc. The numbers denote NCBI database accession numbers; that outside parentheses is an amino acid sequence number, and that inside parentheses is abase sequence number).

Since there is a possibility of the occurrence of a mutation of a gene sequence or an amino acid sequence between biological individuals that does not impair the physiological function of a protein, GST-π and GSTP1 gene, and Akt and Akt gene in the present invention are not limited to proteins or nucleic acids having the same sequence as the above known sequences, and can include those that have a sequence that is different from the above sequence by one or more amino acids or bases, typically one or a few, for example, one, two, three, four, five, six, seven, eight, nine, or ten amino acids or bases, but have an equivalent function to that of the known GST-π and Akt. The specific functions of GST-π and Akt are as described later.

In the present specification, phrases such as 'when used herein', 'used herein', 'in the present specification', and 'described herein' mean, unless otherwise specified, that the description following them applies to all of the inventions described in the present specification. Furthermore, unless otherwise defined, all of the technical terms and scientific terms used herein have the same meaning as that usually understood by a person skilled in the art. The entireties of all of the patents, patent publications, and other publications referred to herein are incorporated herein by reference.

Examples of the 'drug that suppresses GST-π ' used herein include, but are not limited to, a drug that suppresses GST-π production and/or activity and a drug that promotes GST-π degradation and/or inactivation. Examples of the drug that suppresses GST-π production include, but are not limited to, an RNAi molecule, ribozyme, antisense nucleic acid, or DNA/RNA chimera polynucleotide for DNA encoding GST-π, or a vector expressing same.

Examples of the drug that suppresses GST-π activity include, but are not limited to, a substance that binds to GST-π such as, for example, glutathione, a glutathione analog (e.g., those described in WO 95/08563, WO 96/40205, WO 99/54346, Non-Patent Document 4, etc.), ketoprofen (Non-Patent Document 2), indomethacin (Hall et al., Cancer Res. 1989; 49 (22): 6265-8), ethacrynic acid, Piriprost (Tew et al., Cancer Res. 1988; 48 (13): 3622-5), an anti-GST-π antibody, and a GST-π dominant negative mutant. These drugs are either commercially available or may be produced appropriately based on known techniques.

The drug that suppresses GST-π production or activity is preferably an RNAi molecule, ribozyme, antisense nucleic acid, or DNA/RNA chimera polynucleotide for DNA encoding GST-π, or a vector expressing same, in terms of high specificity and a low possibility of side effects.

Suppression of GST-π may be determined by the expression or activity of GST-π in cells being suppressed compared with a case in which a GST-π suppressing agent is not utilized. Expression of GST-π may be evaluated by any known technique; examples thereof include, but are not limited to, an immunoprecipitation method utilizing an anti-GST-π antibody, EIA, ELISA, IRA, IRMA, a western blot method, an immunohistochemical method, an immunocytochemical method, a flow cytometry method, various hybridization methods utilizing a nucleic acid that specifically hybridizes with a nucleic acid encoding GST-π or a unique fragment thereof, or a transcription product (e.g., mRNA) or splicing product of said nucleic acid, a northern blot method, a Southern blot method, and various PCR methods.

Furthermore, the activity of GST-π may be evaluated by analyzing a known activity of GST-π including, but not limited to, binding to a protein such as, for example, Raf-1 (in particular phosphorylated Raf-1) or EGFR (in particular phosphorylated EGFR) by means of any known method such as for example an immunoprecipitation method, a western blot method, amass analysis method, a pull-down method, or a surface plasmon resonance (SPR) method.

Examples of the 'drug that suppresses Akt' used herein include, but are not limited to, a drug that suppresses Akt production and/or activity and a drug that promotes Akt degradation and/or inactivation. Examples of the drug that suppresses Akt production include, but are not limited to, an RNAi molecule, ribozyme, antisense nucleic acid, or DNA/RNA chimera polynucleotide for DNA encoding Akt, or a vector expressing same.

Examples of the drug that suppresses Akt activity include, but are not limited to, a substance that binds to Akt such as, for example, Akt Inhibitor from Merck Millipore (Akt Inhibitor, Akt Inhibitor II to XIII), MK-2206, Perifosine, GSK690693, AT7867, CCT128930, PHT-427, Palomid 529, PF-04691502, triciribine, triciribine phosphate (NSC-280594), A-674563, sc-221226, an anti-Akt antibody, and an Akt dominant negative mutant. These drugs are either commercially available or may be produced appropriately based on known techniques.

The drug that suppresses Akt production or activity is preferably an RNAi molecule, ribozyme, antisense nucleic acid, or DNA/RNA chimera polynucleotide for DNA encoding Akt, or a vector expressing same, in terms of high specificity and a low possibility of side effects.

Suppression of Akt may be determined by the expression or activity of Akt in cells being suppressed compared with a case in which an Akt-suppressing agent is not utilized. Expression of Akt may be evaluated by any known technique; examples thereof include, but are not limited to, an immunoprecipitation method utilizing an anti-Akt antibody, EIA, ELISA, IRA, IRMA, a western blot method, an immunohistochemical method, an immunocytochemical method, a flow cytometry method, various hybridization methods utilizing a nucleic acid that specifically hybridizes with a nucleic acid encoding Akt or a unique fragment thereof, or a transcription product (e.g., mRNA) or splicing product of said nucleic acid, a northern blot method, a Southern blot method, and various PCR methods.

Furthermore, the activity of Akt may be evaluated by analyzing a known activity of Akt including, but not limited to, binding to a protein such as, for example, mTOR by means of any known method such as for example an immunoprecipitation method, a western blot method, a mass analysis method, a pull-down method, or a surface plasmon resonance (SPR) method.

When used herein, the RNAi molecule denotes any molecule that causes RNA interference, including, but not limited to, a duplex RNA such as siRNA (small interfering RNA), miRNA (micro RNA), shRNA (short hairpin RNA), ddRNA (DNA-directed RNA), piRNA (Piwi-interacting RNA), or rasiRNA (repeat associated siRNA) and modified forms thereof. These RNAi molecules may be commercially available or may be designed and prepared based on known sequence information, etc.

Furthermore, when used herein, the antisense nucleic acid includes RNA, DNA, PNA, or a complex thereof.

When used herein, the DNA/RNA chimera polynucleotide includes, but is not limited to, a double-strand polynucleotide composed of DNA and RNA that inhibits the expression of a target gene described in for example JP, A, 2003-219893.

The drug that suppresses GST-π and the drug that suppresses Akt may be contained in a single formulation or may be contained separately in two or more formulations. In the case of the latter, each formulation may be administered at the same time or they may be administered with a time interval therebetween. When administered with a time interval therebetween, the formulation containing a drug that suppresses GST-π may be administered prior to the formulation containing a drug that suppresses Akt or may be administered subsequent thereto.

The present invention also relates to an agent or composition for enhancing the induction of apoptosis and/or the suppression of cell proliferation (hereinafter, also called an 'apoptosis-induction enhancing agent', a 'cell proliferation-suppression enhancing agent', an 'apoptosis-induction enhancing composition' or a 'cell proliferation-suppression enhancing composition') by a drug that suppresses GST-π, the agent or composition containing as an active ingredient a drug that suppresses Akt.

The amount of active ingredient formulated in the agent or composition of the present invention may be an amount that induces apoptosis and/or suppresses cell proliferation when the agent or composition is administered. Furthermore, it is preferably an amount that does not cause an adverse effect that exceeds the benefit of administration. Such an amount is known or may be determined appropriately by an in vitro test using cultured cells, etc., or a test in a model animal such as a mouse, a rat, a dog, or a pig, and such test methods are well known to a person skilled in the art. Induction of apoptosis may be evaluated by various known techniques, for example, by detection of an apoptosis-specific phenomenon such as DNA fragmentation, binding of annexin V to cell membrane, change in mitochondrial membrane potential, or activation of caspase, or by TUNEL staining. Furthermore, suppression of cell proliferation may be evaluated by various known methods, for example, counting of the number of living cells over time, measurement of the size, volume, or weight of a tumor, measurement of the amount of DNA synthesized, the WST-1 method, the BrdU (bromodeoxyuridine) method, or the $^3$H thymidine incorporation method. The amount of active ingredient formulated can vary according to the manner in which the agent or composition is administered. For example, when a plurality of units of the composition is used for one administration, the amount of active ingredient to be formulated in one unit of the composition may be determined by dividing the amount of active ingredient necessary for one administration by said plurality of units. Adjustment of such a formulation amount can be carried out appropriately by a person skilled in the art.

The present invention also relates to a process for producing an agent or composition for inducing apoptosis or suppressing cell proliferation, the process comprising formulating as active ingredients a drug that suppresses GST-π and a drug that suppresses Akt; use of a drug that suppresses GST-π and a drug that suppresses Akt in the production of an agent or composition for inducing apoptosis or suppressing cell proliferation; a combination of a drug that suppresses GST-π and a drug that suppresses Akt for use in the induction of apoptosis or the suppression of cell proliferation; and a method for inducing apoptosis or suppressing cell proliferation comprising administering effective amounts of a drug that suppresses GST-π and a drug that suppresses Akt.

The present invention also relates to a process for producing an agent or composition for enhancing the induction of apoptosis or the suppression of cell proliferation by a drug that suppresses GST-π, the process comprising formulating as an active ingredient a drug that suppresses Akt; use of a drug that suppresses Akt in the production of an agent or composition for enhancing the induction of apoptosis or the suppression of cell proliferation by a drug that suppresses GST-π; a drug that suppresses Akt for use in enhancing the induction of apoptosis or the suppression of cell proliferation by a drug that suppresses GST-π; and a method for enhancing the induction of apoptosis or the suppression of cell proliferation by a drug that suppresses GST-π, the method comprising administering an effective amount of a drug that suppresses Akt.

The drug or the formulation amount thereof in the above-mentioned production process or use are as described above. Formulation of each drug may be carried out in accordance with any known technique.

All of the above methods for inducing apoptosis or suppressing cell proliferation may be either an in vitro method or an in vivo method. Furthermore, the drugs in the methods are as described above, and the effective amount of drug may be an amount that induces apoptosis or suppresses cell proliferation in cells to which it is administered. It is also preferably an amount that does not cause an adverse effect that exceeds the benefit of administration. Such an amount is known or may be determined appropriately by an in vitro test using cultured cells, etc., and such a test method is well known to a person skilled in the art. Induction of apoptosis or suppression of cell proliferation may be evaluated by various known techniques, including those described above. The effective amount above need not necessarily be one that effects apoptosis or suppression of cell proliferation in all the cells of a cell population to which the drug is administered. For example, the effective amount above may be an amount that effects apoptosis or suppression of cell proliferation in, of the cell population, at least 1% of the cells, at least 2%, at least 3%, at least 4%, at least 5%, at least 6%, at least 8%, at least 10%, at least 12%, at least 15%, at least 20%, at least 25%, etc.

The apoptosis-inducing and cell proliferation-suppressing agent of the present invention can induce apoptosis and suppression of proliferation effectively even in cells having an abnormality in cell proliferation, etc., and is effective as a component of a pharmaceutical composition. Therefore, one aspect of the present invention includes a pharmaceutical composition containing the apoptosis-inducing and cell proliferation-suppressing agent of the present invention.

The pharmaceutical composition of the present invention is effective in treating a disease in which there is abnormal apoptosis in particular. Therefore, one embodiment of the present invention relates to a pharmaceutical composition for treating a disease in which there is abnormal apoptosis, the pharmaceutical composition containing the apoptosis-inducing agent. When used herein, examples of the disease in which there is abnormal apoptosis include, but are not limited to, a disease due to abnormal cell proliferation, a disease due to KRAS mutation, and a disease due to GST-π overexpression. Examples of the disease due to abnormal cell proliferation include, but are not limited to, a benign or malignant tumor, hyperplasia, keloid, Cushing's syndrome, primary aldosteronism, erythroplakia, polycythemia vera, leukoplakia, hyperplastic scar, lichen planus, and lentiginosis. Examples of the disease due to KRAS mutation include, but are not limited to, a benign or malignant tumor (also called a cancer or a malignant neoplasm). Examples of the disease due to GST-π overexpression include, but are not limited to, a benign or malignant tumor, in particular a drug-resistant malignant tumor (e.g., resistant to an alkylating agent such as melphalan or cyclophosphamide, an anthracycline-based antitumor antibiotic such as adriamycin, a platinum complex such as cisplatin, etoposide, etc.). In one embodiment of the present invention, the disease in which there is abnormal apoptosis is a cancer.

Examples of the cancer in the present invention include, but are not limited to, sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma, carcinomas such as brain tumor, head and neck carcinoma, breast carcinoma, lung carcinoma, esophageal carcinoma, gastric carcinoma, duodenal carcinoma, appendiceal carcinoma, colon carcinoma, rectal carcinoma, liver carcinoma, pancreatic carcinoma, gallbladder carcinoma, bile duct carcinoma, anal carcinoma, renal carcinoma, ureteral carcinoma, bladder carcinoma, prostate carcinoma, penile carcinoma, testicular carcinoma, uterine carcinoma, ovarian carcinoma, vulvar carcinoma, vaginal carcinoma, and skin carcinoma and, furthermore, leukemia and malignant lymphoma. In the present invention, 'cancer' includes epithelial malignancy and non-epithelial malignancy. The cancer in the present invention can be present at any site of the body, for example, the brain, head and neck, chest, limbs, lung, heart, thymus, esophagus, stomach, small intestine (duodenum, jejunum, ileum), large intestine (colon, cecum, appendix, rectum), liver, pancreas, gallbladder, anus, kidney, urinary duct, bladder, prostate, penis, testis, uterus, ovary, vulva, vagina, skin, striated muscle, smooth muscle, synovial membrane, cartilage, bone, thyroid, adrenal gland, peritoneum, mesentery, bone marrow, blood, vascular system, lymphatic system such as lymph node, lymphatic fluid, etc.

In one embodiment of the present invention, the cancer includes cancer cells having the mutated KRAS defined above. In one embodiment of the present invention, the cancer includes cancer cells that exhibit hormone- or growth factor-independent proliferation. In one embodiment of the present invention, the cancer includes cancer cells exhibiting GST-π overexpression. In one embodiment of the present invention, the cancer is drug resistant. In one embodiment of the present invention, the cancer has resistance to a drug selected from the group consisting of an alkylating agent such as melphalan or cyclophosphamide, an anthracycline-based antitumor antibiotic such as adriamycin, a platinum complex such as cisplatin, and etoposide. In one embodiment of the present invention, the cancer has resistance to a medicinal agent selected from the group consisting of melphalan, cyclophosphamide, adriamycin, cisplatin, and etoposide.

The present invention also relates to a pharmaceutical composition for treating a disease in which there is abnormal apoptosis, the composition containing as active ingredients a drug that suppresses GST-π and a drug that suppresses Akt; a process for producing a pharmaceutical composition for treating a disease in which there is abnormal apoptosis, the process comprising formulating as active ingredients a drug that suppresses GST-π and a drug that suppresses Akt; use of a drug that suppresses GST-π and a drug that suppresses Akt for the production of a pharmaceutical composition for treating a disease in which there is abnormal apoptosis; a combination of a drug that suppresses GST-π and a drug that suppresses Akt for use in the treatment of a disease in which there is abnormal apoptosis; and a method for treating a disease in which there is abnormal apoptosis, the method comprising administering an effective amount of the pharmaceutical composition to a subject that requires same.

The drug, the formulation amount, and the disease in which there is abnormal apoptosis in the above production process or use are as already described. Formulation of each drug may be carried out in accordance with any known technique.

The apoptosis-inducing agent, the cell proliferation inhibitor, and the composition containing same of the present invention may be used in a combination with another active ingredient. Here, being used in combination includes for example administering another active ingredient as a separate formulation, and administering another active ingredient as a mixture with at least one type of other medicinal agent. When administering as a separate formulation, a formulation containing another active ingredient may be administered prior to, at the same time as, or subsequent to another formulation.

Examples of such an active ingredient include one that is effective in treating a disease as a target. For example, when a disease to be treated is a cancer, an anticancer drug may be used in combination. Examples of the anticancer drug include an alkylating agent such as ifosfamide, nimustine hydrochloride, cyclophosphamide, dacarbazine, melphalan, or ranimustine, a metabolism antagonist such as gemcitabine hydrochloride, enocitabine, cytarabine ocfosfate, a cytarabine formulation, a tegafur/uracil or tegafur/gimeracil/oteracil potassium combination drug (e.g., TS-1), doxifluridine, hydroxycarbamide, fluorouracil, methotrexate, or mercaptopurine, an antitumor antibiotic such as idarubicin hydrochloride, epirubicin hydrochloride, daunorubicin hydrochloride, daunorubicin citrate, doxorubicin hydrochloride, pirarubicin hydrochloride, bleomycin hydrochloride, peplomycin sulfate, mitoxantrone hydrochloride, or mitomycin C, an alkaloid such as etoposide, irinotecan hydrochloride, vinorelbine tartarate, docetaxel hydrate, paclitaxel, vincristine sulfate, vindesine sulfate, or vinblastine sulfate, a hormonal therapeutic drug such as anastrozole, tamoxifen citrate, toremifene citrate, bicalutamide, flutamide, or estramustine phosphorate, a platinum complex such as carboplatin, cisplatin (CDDP), or nedaplatin, an angiogenesis inhibitor such as thalidomide, neovastat, or bevacizumab, and L-asparaginase.

Other examples of said other active ingredient include a drug that suppresses autophagy. When used herein, autophagy can include macroautophagy, microautophagy, chaperone-mediated autophagy, etc., but typically means macroautophagy. Therefore, the term 'autophagy' in the present invention refers to 'macroautophagy' unless otherwise specified.

Autophagy, meaning 'self-devouring', is one of the intracellular protein degradation mechanisms, and is in charge of the degradation and recycling of protein within a cell. Autophagy is seen in a wide variety of biological species including yeasts and mammals and is generally accompanied by a series of processes including (a) formation of a PAS (phagophore assembly site), (b) elongation and extension of the phagophore (isolation membrane) surrounding a protein to be degraded and formation of an autophagosome encapsulating the protein to be degraded thereby, (c) formation of an autolysosome by fusion of an autophagosome and a lysosome, and (d) degradation of the protein within the autolysosome.

The above processes (a) to (c) involve specific autophagy-related factors. With regard to the autophagy-related factors, the first research was carried out with yeast, and a large number, including ATG1 to ATG27, have been identified so far (Klionsky et al., Dev Cell. 2003; 5 (4): 539-45); research with mammals has also advanced, a plurality of homologs have been identified, and the core molecular mechanism of autophagy is becoming clear (Yang and Klionsky, Curr Opin Cell Biol. 2010; 22 (2): 124-31).

Examples of autophagy-related factors involved in the core molecular mechanism of autophagy in mammals include those involved in formation of PAS, such as VMP1, TP53INP2, mAtg9, the ULK complex (composed of ULK1, ULK2, mAtg13, and FIP200), the PI3K complex (the Atg14L complex composed of Beclinl, hVps34, p150, Ambral, and Atg14L, and the UVRAG complex composed of Beclinl, hVps34, p150, Bif-1, and UVRAG) and those involved in phagophore elongation such as LC3-II and the Atg12-Atg5-Atg16L complex.

Therefore, examples of the drug that suppresses autophagy include, but are not limited to, a drug that suppresses the production and/or activity of an autophagy-related factor such as those described above and a drug for promoting the degradation and/or inactivation of an autophagy-related factor (when the related factor is a complex, not only the complex itself but individual components forming same are also included). Examples of the drug that suppresses the production of an autophagy-related factor include an RNAi molecule, ribozyme, antisense nucleic acid, or DNA/RNA chimera polynucleotide for DNA encoding an autophagy-related factor, or a vector expressing same.

Examples of the drug that suppresses the activity of an autophagy-related factor include, but are not limited to, a PI3K inhibitor (e.g., wortmannin, etc.), in particular a class III PI3K inhibitor (e.g., 3-MA (3-methyladenine), etc.), a substance that inhibits fusion of an autophagosome and a lysosome (e.g., bafilomycin A1, etc.), a substance that inhibits protein degradation in an autolysosome (e.g., chloroquine, leupeptin, etc.), a substance that binds to an autophagy-related factor (e.g., an antibody for an autophagy-related factor, etc.), and a dominant negative mutant of an autophagy-related factor. These drugs are commercially available or may be produced appropriately based on known techniques.

From the viewpoint of high specificity and low side effects, the drug that suppresses autophagy is preferably an RNAi molecule, ribozyme, antisense nucleic acid, or DNA/RNA chimera polynucleotide for DNA encoding an autophagy-related factor, or a vector expressing same.

Suppression of autophagy may be determined by observing that autophagy is suppressed in cells compared with a case in which the autophagy-suppressing agent of the present invention is not utilized. Inhibition of autophagy may be evaluated based on any known technique, examples of which include, but are not limited to, detection of an autophagosome by an electron microscopy method, and detection of an autophagy marker (e.g., Atg5, Atg12, LC3, in particular LC3-II, etc.). LC3-II may be detected by, for example, without being limited to, using a specific antibody for LC3-II, or may be detected by subjecting a sample to separation with electrophoresis, etc., and then detecting LC3-II, separated as a band that is different from LC3-I, by a western blot method, etc., using an antibody that reacts with LC3-II or both LC3-I and LC3-II. Furthermore, because LC3-I is dispersed within the cytoplasm while LC3-II is localized in an autophagy-specific structure such as an isolation membrane, an autophagosome, or an autolysosome, the presence or number of spot-like signals showing these structures, which are manifested by immunostaining, etc., with an antibody that reacts with LC3-II (including an antibody that reacts to both LC3-I and LC3-II) may be used as an indicator for autophagy.

The present invention also relates to an agent or composition for suppressing autophagy in cells in which GST-π is suppressed (also called an 'autophagy-suppressing agent' or an 'autophagy-suppressing composition'), the agent or composition containing as an active ingredient a drug that suppresses Akt.

In the present invention, suppression of autophagy may be determined by autophagy being suppressed in cells compared with a case in which the agent or composition of the present invention is not utilized. The technique for evaluating autophagy is as described above.

When used herein, 'GST-π being suppressed' includes for example a state in which GST-π is being suppressed in cells expressing GST-π. Examples of such a state include a state in which a drug that suppresses GST-π (e.g., those described above, etc.) has been administered to cells expressing GST-π.

Whether or not GST-π is being expressed in certain cells is either known from the literature or may be determined by actually detecting the expression of GST-π in cells. Expression of GST-π may be detected by any known technique, including those described above.

The present invention further relates to a process for producing an agent or composition for suppressing autophagy in cells in which GST-π is suppressed, the process comprising a step of formulating a drug that suppresses Akt; use of a drug that suppresses Akt in the production of an agent or composition for suppressing autophagy in cells in which GST-π is suppressed; a drug that suppressed Akt for use in the suppression of autophagy in cells in which GST-π is suppressed; and a method for suppressing autophagy in cells in which GST-π is suppressed, the method comprising administering an effective amount of a drug that suppresses Akt.

The agent or composition for suppressing autophagy of the present invention is useful in the treatment of a state associated with enhanced autophagy under conditions in which GST-π is suppressed. Examples of such a state include, but are not limited to, a state in which expression or activation of GST-π is degraded and a state in which a drug that suppresses expression or activation of GST-π is administered.

Therefore, the present invention also relates to a pharmaceutical composition for treating a state associated with enhanced autophagy under conditions in which GST-π is suppressed, the composition containing as an active ingredient a drug that suppresses Akt; a process for producing a pharmaceutical composition for treating a state associated with enhanced autophagy under conditions in which GST-π is suppressed, the process comprising a step of formulating a drug that suppresses Akt; use of a drug that suppresses Akt in the production of a pharmaceutical composition for treating a state associated with enhanced autophagy under conditions in which GST-π is suppressed; a drug suppressing Akt for use in the treatment of a state associated with enhanced autophagy under conditions in which GST-π is suppressed; a method for treating a state associated with enhanced autophagy under conditions in which GST-π is suppressed, the method comprising administering an effective amount of a drug that suppresses Akt to a subject requiring same.

The formulation amount of the active ingredient in the agent or composition of the present invention related to the suppression of autophagy may be an amount that achieves suppression of autophagy when the agent or composition is administered. Furthermore, it is preferably an amount that does not cause an adverse effect that exceeds the benefit of administration. Such an amount is known or may be determined appropriately by means of an in vitro test using cultured cells, etc., or a test in a model animal such as a mouse, a rat, a dog, or a pig, and such a test method is well known to a person skilled in the art. Suppression of autophagy may be evaluated by various known techniques, including those described above. The formulation amount of active ingredient can vary according to the mode of administration of the agent or composition. For example, when a plurality of units of the composition is used for one administration, the amount of active ingredient to be formulated in one unit of the composition may be one obtained by dividing the amount of active ingredient necessary for one administration by said plurality of units. Adjustment of such a formulation amount can be carried out appropriately by a person skilled in the art.

The drug and the formulation amount thereof in the production process or use of the agent or composition related to suppression of autophagy are as described above. Formulation of each drug may be carried out in accordance with any known technique.

All of the methods related to suppression of autophagy may be an in vitro method or an in vivo method. Furthermore, the effective amount of drug in the above methods may be an amount that achieves a desired effect (i.e., suppression of autophagy) in cells to which it is administered. Moreover, it is preferably an amount that does not cause an adverse effect that exceeds the benefit of administration. Such an amount is known or may be determined appropriately by an in vitro test, etc., using cultured cells, etc., and such a test method is well known to a person skilled in the art. Achievement of a desired effect may be evaluated by various known techniques, including those described above. The effective amount above need not necessarily be one that induces a desired effect in all the cells of a cell population to which the drug is administered. For example, the effective amount above may be an amount that induces a desired effect in, of the cell population, at least 1% of cells, at least 2%, at least 3%, at least 4%, at least 5%, at least 6%, at least 8%, at least 10%, at least 12%, at least 15%, at least 20%, at least 25%, etc.

When the active ingredient in the various agents or compositions, treatment methods, etc., of the present invention described herein is a nucleic acid, for example, an RNAi molecule, a ribozyme, an antisense nucleic acid, a DNA/RNA chimera polynucleotide, etc., it may be used as a naked nucleic acid as it is, but may also be carried by various vectors. As the vector, any known vector such as a plasmid vector, a phage vector, a phagemid vector, a cosmid vector, or a virus vector may be used. The vector preferably contains at least a promoter that enhances expression of the nucleic acid carried, and in this case the nucleic acid is preferably operably linked to such a promoter. The nucleic acid being operably linked to a promoter referred to herein means that the nucleic acid and the promoter are positioned so that a protein encoded by the nucleic acid is appropriately produced by the action of the promoter. The vector may or may not be replicable in a host cell, and the transcription of a gene may be carried out either outside the nucleus or within the nucleus of a host cell. In the latter case, the nucleic acid may be incorporated into the genome of a host cell.

Furthermore, the active ingredient may be carried by various non-viral lipid or protein carriers. Examples of such carriers include, but are not limited to, cholesterol, a liposome, an antibody protomer, cyclodextrin nanoparticles, a fusion peptide, an aptamer, a biodegradable polylactic acid copolymer, and a polymer; the efficiency of incorporation into cells can be enhanced (see, e.g., Pirollo and Chang, Cancer Res. 2008; 68 (5): 1247-50, etc.). In particular, a cationic liposome or a polymer (e.g., polyethyleneimine, etc.) is useful. Further examples of useful polymers as such a carrier include those described in US 2008/0207553, US 2008/0312174, etc.

With regard to the various pharmaceutical compositions of the present invention described herein, the active ingredient may be combined with another optional component as long as the effect of the active ingredient is not impaired. Examples of such an optional component include another chemical therapeutic agent, a pharmacologically acceptable carrier, an excipient, a diluent, etc. Furthermore, depending on the route of administration, the mode of drug release, etc., the composition may be coated with an appropriate material such as for example an enteric coating or a timed disintegration material, or may be incorporated into an appropriate drug release system.

The various agents and compositions (including the various pharmaceutical compositions) of the present invention described herein may be administered via various routes including both oral and parenteral routes, for example, without limitation, oral, intravenous, intramuscular, subcutaneous, local, intratumoral, rectal, intraarterial, intraportal, intraventricular, transmucosal, transdermal, intranasal, intraperitoneal, intrapulmonary, and intrauterine routes, and may be formulated into a dosage form suitable for each administration route. With regard to such dosage forms and formulation methods, any known form or method may be employed appropriately (see, e.g., Hyojun yakuzaigaku (Standard Pharmaceutical Science), Ed. by Yoshiteru Watanabe et al., Nankodo, 2003, etc.).

Examples of the dosage form suitable for oral administration include, but are not limited to, a powder, granules, a tablet, a capsule, a liquid, a suspension, an emulsion, a gel, and a syrup, and examples of the dosage form suitable for parenteral administration include an injection such as a solution injection, a suspension injection, an emulsion injection, or an injection in a form that is prepared at the time of use. A formulation for parenteral administration may be in the form of an aqueous or nonaqueous isotonic sterile solution or suspension.

The various agents or compositions (including various pharmaceutical compositions) of the present invention described herein may be targeted at a specific tissue or cells. Targeting may be achieved by any known technique. When delivery to a cancer is attempted, for example, without limitation, a technique such as passive targeting in which a formulation is made into a size of 50 to 200 µm in diameter, in particular 75 to 150 µm, etc., which is suitable for exhibition of an EPR (enhanced permeability and retention) effect, or active targeting in which a ligand of CD19, HER2, a transferrin receptor, a folic acid receptor, a VIP receptor, EGFR (Torchilin, AAPS J. 2007; 9 (2): E128-47), RAAG10 (JP, A (PCT) 2005-532050), PIPA (JP, A (PCT) 2006-506071), or KIDS (JP, A (PCT) 2007-529197), etc., a peptide having an RGD motif or an NGR motif, F3, LyP-1 (Ruoslahti et al., J Cell Biol. 2010; 188 (6): 759-68), etc., is used as a targeting agent may be used. Furthermore, since a retinoid or a derivative thereof is known to be useful as a targeting agent for cancer cells (WO 2008/120815), a carrier containing a retinoid as a targeting agent may also be used. Such carriers are described in the literature above as well as in WO 2009/036368, WO 2010/014117, WO 2012/170952, etc.

The various agents or compositions (including various pharmaceutical compositions) of the present invention described herein may be supplied in any form, and from the viewpoint of storage stability, may be provided in a form that can be prepared at the time of use, for example, a form that allows a doctor and/or pharmacist, a nurse, another paramedic, etc., to prepare it at the medical site or its vicinity. Such a form is particularly useful when the agent or composition of the present invention contains a component that is difficult to store stably, such as a lipid, a protein, or a nucleic acid. In this case, the agent or composition of the present invention is provided in one or more containers containing at least one of the essential constituents, and preparation is carried out prior to use, for example, within 24 hours, preferably within 3 hours, and more preferably immediately before use. When carrying out preparation, a reagent, a solvent, preparation equipment, etc., that are usually available at a place of preparation may be used as appropriate.

Therefore, the present invention also relates to a kit for preparing a composition, the kit containing one or more containers, the container singly or in combination containing active ingredients to be contained in the various agents or compositions of the present invention; and essential constituents of the various agents or compositions provided in the form of such a kit. The kit of the present invention may include, in addition to the above, instructions such as a written explanation or an electronic recording medium such as a CD or DVD describing a preparation method, an administration method, etc., for the various agents or compositions of the present invention. Furthermore, the kit of the present invention may contain all of the constituents for completing the various agents or compositions of the present invention, but need not necessarily contain all of the constituents. Therefore, the kit of the present invention need not contain a reagent or a solvent that is usually available at a medical site, an experimental laboratory, etc., such as sterile water, physiological saline, or a glucose solution.

The effective amount in the various treatment methods of the present invention described herein is for example an amount that reduces symptoms of a disease or delays or stops the progress of a disease, and is preferably an amount that suppresses or cures a disease. It is also preferably an amount that does not cause an adverse effect that exceeds the benefit of administration. Such an amount may be determined appropriately by an in vitro test using cultured cells, etc., or a test in a model animal such as a mouse, a rat, a dog, or a pig, and such test methods are well known to a person skilled in the art. Furthermore, the dose of a drug used in the treatment method of the present invention is known to a person skilled in the art or may be determined appropriately by the tests described above, etc.

The specific dose of the active ingredient to be administered in the treatment method of the present invention described herein can be determined by taking into consideration various conditions related to the subject that requires treatment, such as for example the seriousness of symptoms, the general health state of the subject, age, body weight, the gender of the subject, diet, the timing and frequency of administration, concomitant pharmaceuticals, the responsiveness to the treatment, the dosage form, and compliance with the treatment.

Examples of the administration route include various routes, including both oral and parenteral routes, such as oral, intravenous, intramuscular, subcutaneous, local, intratumoral, rectal, intraarterial, intraportal, intraventricular, transmucosal, transdermal, intranasal, intraperitoneal, intrapulmonary, and intrauterine routes.

The frequency of administration depends on the properties of the agent or composition used and the condition of the subject, including those described above, and may be a plurality of times a day (that is, two, three, four, five, or more times a day), once a day, every few days (that is, every two, three, four, five, six, seven days, etc.), every week, every few weeks (that is, every two, three, four weeks, etc.), etc.

When used herein, the term 'subject' means any biological individual and is preferably an animal, more preferably a mammal, and yet more preferably a human individual. In the present invention, the subject may be either healthy or affected by some disease, but when an attempt is made to treat a specific disease, it typically means a subject affected by such a disease or having a risk of being affected.

Furthermore, when used herein, the term 'treatment' includes all types of preventive and/or therapeutic interventions medically allowed for the purpose of cure, temporary remission, prevention, etc., of a disease. For example, the term 'treatment' includes medically allowable interventions for various types of purposes including delaying or stopping the progress of a disease, making a lesion regress or disappear, preventing onset, or inhibiting recurrence.

EXAMPLES

The present invention is explained in further detail below by reference to Examples, but they are only illustrations and should not be construed as limiting the present invention.

Example 1: Knockdown of GST-π and Akt by siRNA $1\times10^6$ PANC-1 cells were plated on a 10 cm dish, and culturing was carried out in Roswell Park Memorial Institute 1640 (RPMI 1640, Sigma), to which 10% fetal bovine serum (Fetal bovine serum, FBS) and 5% L-glutamine were added, for 18 hours. Culturing conditions were 37° C. and 5% $CO_2$ unless otherwise specified. Furthermore, $1\times10^6$ A549 cells were plated on a 10 cm dish, and culturing was carried out in Dulbecco's modified Eagle's medium (DMEM, Sigma), to which 10% FBS and 10% L-glutamine were added, for 18 hours. The respective media were replaced, and 2 hours later 20% to 30% confluent PANC-1 or A549 cells were transfected with GST-π siRNA and/or Akt siRNA using Lipofectamine RNAiMAX (Life Technologies).

A Lipofectamine/siRNA mixed solution for transfection was prepared as follows. First, 35 μL of Lipofectamine RNAiMAX and 965 μL of OPTI-MEM (Sigma) were mixed to thus prepare a Lipofectamine solution. Subsequently, a predetermined amount of 10 μM siRNA was diluted to 1 mL with OPTI-MEM to thus prepare an siRNA solution (for example, when preparing a siRNA solution having a final concentration of 30 nM for use, 36 μL of 10 μM siRNA and 964 μL of OPTI-MEM were mixed), and this was mixed with the lipofectamine solution and allowed to stand at room temperature for 15 minutes. As siRNA one below was used. GST-π siRNA:

```
                              (SEQ ID No: 1)
Sense chain:      GGGAGGCAAGACCUUCAUUtt (SEQ ID No: 2)
Antisense chain:  AAUGAAGGUCUUGCCUCCCtg
```

(Uppercase letters indicate RNA and lowercase letters indicate DNA) Akt siRNA: Akt siRNA I (Cell Signaling Technology, #6211) Control siRNA: AllStars Neg. Control siRNA 1027281 (QIAGEN)

In order to optimize the concentration of siRNA, a final concentration of 10 to 50 nM of GST-π siRNA or Akt siRNA was added to a dish containing PANC-1 cells or A549 cells flushed with 10 mL of PTI-MEM, culturing was carried out at room temperature for 5 hours, the medium was replaced (RPMI 1640 containing 5% FBS for PANC-1 cells and DMEM containing 10% FBS for A549 cells), and culturing was carried out for 2 hours. As a control, one to which a final concentration of 30 nM of Control siRNA was added was used. These cells were detached by treatment with trypsin and harvested from the 10 cm dish, and replated on 6 cm dishes at $1\times10^5$ cells each. Subsequently, every 24 hours, the cells were detached by treatment with trypsin and harvested from the dish, and the number of cells was counted. The results obtained 4 days after transfection are shown in FIGS. 1 and 2. It can be seen from these results that the cell proliferation inhibition effect by each siRNA almost reaches a plateau at a final concentration of 30 nM.

In order to test the effect when GST-π siRNA and Akt siRNA are made to act at the same time, a Lipofectamine/siRNA mixed solution in which GST-π siRNA and Akt siRNA were mixed was added to each of the cells in the same way as above, and the number of cells was counted. As a control, one to which a final concentration of 30 nM of Control siRNA was added was used. The Lipofectamine/siRNA mixed solution was prepared by the same method as above using a mixture of 36 μL of 10 μM GST-π siRNA, 36 μL of 10 μM Akt siRNA, and 928 μL of OPTI-MEM as an siRNA solution. From the results shown in FIGS. 3 and 4, it can be seen that when both GST-π and Akt were knocked down, the cell proliferation-suppressing effect became larger compared with a case in which only one thereof was knocked down.

Furthermore, with regard to cell morphology being examined, when GST-π was knocked down, there were 20% to 30% of cells that had enlarged and did not proliferate. In particular, for PANC-1, in addition to enlargement, there were a large number of floating cells (dead cells). When Akt was knocked down, there were a large number of dead cells. When GST-π and Akt were both knocked down, compared with a case in which one thereof was knocked down, the number of dead cells increased for both PANC-1 and A549. From these findings it is suggested that apoptosis is induced by knockdown of GST-π or Akt, and when both are knocked down, apoptosis is more strongly induced.

Example 2: Combined Use of GST-π siRNA and Akt Inhibitor

In order to find out whether the same results would be obtained by the use of a substance other than siRNA as the Akt inhibitor, a test was carried out using Akt Inhibitor VIII (Merck #124018, 1,3-Dihydro-1-(1-((4-(6-phenyl-1H-imidazo[4,5-g]quinoxalin-7-yl)phenyl)methyl)-4-piperidinyl)-2H-benzimidazol-2-one), which is a small molecule. It is known that Akt Inhibitor VIII binds to a Pleckstrin homology (PH) region of Akt to thus cause allosteric inhibition, and although it does not inhibit Akt3 it selectively blocks activation and phosphorylation of Akt1 and Akt2 (Barnett, S. F., et al. 2005. Biochem. J. 385: 399-408, Lindsley, C. W., et al. 2005. Bioorg. Med. Chem. Lett. 15: 761-764, Zhao, Z., et al. 2005. Bioorg. Med. Chem. Lett. 15: 905-909).

$1\times10^6$ PANC-1 cells were plated on a 10 cm dish, and culturing was carried out in RPMI 1640, to which 10% FBS and 5% L-glutamine were added, for 24 hours. The medium was replaced with 10 mL of OPTI-MEM, GST-π siRNA prepared in the same way as in Example 1 was added to the dish at a final concentration of 50 nM, culturing was carried out at room temperature for 5 hours, the medium was then replaced with RPMI 1640 containing 5% FBS, and culturing was carried out for 2 hours. As a control, one to which Scramble siRNA was added at the same concentration was used. The scramble siRNA used was one having the sequence below (Hokkaido System Science Co., Ltd.).

Sense chain: (SEQ ID No: 3)
CGAUUCGCUAGACCGGCUUCAUUGCAG

Antisense chain: (SEQ ID No: 4)
GCAAUGAAGCCGGUCUAGCGAAUCGAU

These cells were detached by treatment with trypsin and harvested from the 10 cm dish, and replated on 6 cm dishes at $1\times10^5$ cells each, and Akt Inhibitor VIII was added at a final concentration of 1 μM. After that, every 24 hours, the cells were detached by treatment with trypsin and harvested from the dish, and the number of cells was counted. The test employed the Bonferroni/Dunn method. The results are shown in FIG. 5. From these results it can also be seen that the cell proliferation inhibition effect is enhanced by inhibition of both GST-π and Akt even by the use of a substance other than siRNA as the Akt inhibitor compared with a case in which either one of GST-π and Akt is inhibited.

Example 3: Suppression of Autophagy by Double Knockdown of GST-π and Akt

The effect on autophagy of double knockdown of GST-π and Akt was investigated.

$1\times10^6$ PANC-1 cells were plated on a 10 cm dish, and culturing was carried out in RPMI 1640, to which 10% FBS and 5% L-glutamine were added, for 24 hours. The medium was replaced with 10 mL of OPTI-MEM, GST-π siRNA prepared in the same way as in Example 1, Akt siRNA, and a mixed solution of GST-π siRNA and Akt siRNA were added to dishes so that each siRNA had a final concentration of 10 nM, and culturing was carried out at room temperature for 5 hours; the medium was then replaced by RPMI 1640 containing 5% FBS, and culturing was carried out for 3 days. The cells on the dish were washed with ice-cooled PBS, and an ice-cooled Lysis buffer was then added to thus break the cells. The Lysis buffer was prepared by mixing 100 μL of NP-40 Alternative, PROTEIN GRADE® Detergent, 10% Solution, Sterile-Filtered (CALBIOCHEM), 500 μL of 1 M Tris-HCl (pH 7.5), 300 μL of 5 M NaCl, 20 μL of 0.5 M EDTA, and 9.08 μL of sterile water. The cell lysate was collected using a cell scraper and ice-cooled for 30 minutes. During this process, inversion mixing was carried out every 10 minutes. The solution thus obtained was subjected to centrifugation at 15000 rpm and 4° C. for 15 minutes, and the supernatant was collected, thus giving a cell extract. This cell extract was subjected to western blot analysis. A reaction with a transfer membrane was carried out at 4° C. for 16 hours using anti-LC3B antibody (SIGMA) as a primary antibody. Detection of LC3 molecules was carried out using a chemiluminescent reagent after a reaction with HRP-labeled secondary antibody. Whether or not autophagy was induced was evaluated by a shift to LC3 type I (18 kDa) and type II (16 kDa).

From the results shown in FIG. 6, it can be seen that autophagy induced by knockdown of GST-π was almost completely suppressed by simultaneous knockdown of Akt.

---

The invention claimed is:

1. An agent comprising as active ingredients a drug that suppresses GST-π and a drug that suppresses Akt, wherein the drug that suppresses GST-π inhibits GST-π expression by targeting GST-π DNA/RNA, and is an RNAi molecule, a ribozyme, an antisense nucleic acid, a DNA/RNA chimera polynucleotide for DNA encoding GST-π, or a vector expressing any one of the foregoing; and wherein the drug that suppresses Akt inhibits Akt expression by targeting Akt DNA/RNA, and is an RNAi molecule, a ribozyme, an antisense nucleic acid, a DNA/RNA chimera polynucleotide for DNA encoding Akt, or a vector expressing any one of the foregoing.

2. A pharmaceutical composition comprising the agent according to claim 1 and a pharmacologically acceptable carrier.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial sequence
<220> FEATURE:
<223> OTHER INFORMATION: GST-p siRNA sense strand

<400> SEQUENCE: 1
gggaggcaag accuucauut t                                        21

<210> SEQ ID NO 2
<211> LENGTH: 21
<212> TYPE: DNA
<213> ORGANISM: Artificial sequence
<220> FEATURE:
<223> OTHER INFORMATION: GST-p siRNA antisense strand

<400> SEQUENCE: 2
aaugaagguc uugccucccu g                                        21

<210> SEQ ID NO 3
<211> LENGTH: 27
<212> TYPE: RNA
<213> ORGANISM: Artificial sequence
<220> FEATURE:
<223> OTHER INFORMATION: Scramble siRNA sense strand

<400> SEQUENCE: 3
cgauucgcua gaccggcuuc auugcag                                  27

<210> SEQ ID NO 4
<211> LENGTH: 27
```

```
<212> TYPE: RNA
<213> ORGANISM: Artificial sequence
<220> FEATURE:
<223> OTHER INFORMATION: Scramble siRNA antisense strand

<400> SEQUENCE: 4
gcaaugaagc cggucuagcg aaucgau                                             27
```